United States Patent
Katzenmaier et al.

(10) Patent No.: US 6,701,172 B2
(45) Date of Patent: *Mar. 2, 2004

(54) UNIVERSALLY FUNCTIONAL BIOMEDICAL ELECTRODE

(75) Inventors: Kevin R. Katzenmaier, Woodbury, MN (US); Samuel G. Netherly, Afton, MN (US); Hatim M. Carim, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/021,779

(22) Filed: Dec. 12, 2001

(65) Prior Publication Data

US 2002/0072664 A1 Jun. 13, 2002

Related U.S. Application Data

(62) Division of application No. 09/326,778, filed on Jun. 4, 1999, now Pat. No. 6,356,779.

(51) Int. Cl.[7] .................. A61B 5/0408; A61B 18/16; A61N 1/04
(52) U.S. Cl. .................. 600/391; 600/392; 606/32; 607/142; 607/152
(58) Field of Search ................ 600/391, 392; 606/32; 607/149, 152, 129, 142

(56) References Cited

U.S. PATENT DOCUMENTS

| | | | |
|---|---|---|---|
| RE24,906 E | 12/1960 | Ulrich | 206/59 |
| 2,973,286 A | 2/1961 | Ulrich | 117/122 |
| 3,389,827 A | 6/1968 | Abere et al. | 220/53 |
| 3,976,055 A | 8/1976 | Monter et al. | 128/2.06 E |
| 4,112,213 A | 9/1978 | Waldman | 526/279 |

(List continued on next page.)

FOREIGN PATENT DOCUMENTS

| | | |
|---|---|---|
| EP | 0051935 | 5/1982 |
| EP | 0 327 304 A1 | 8/1989 |
| WO | WO 94/12585 | 6/1994 |
| WO | WO 95/20634 | 8/1995 |
| WO | WO 95/27016 | 10/1995 |
| WO | WO 97/24149 | 7/1997 |
| WO | WO 97/24376 | 7/1997 |
| WO | WO 97/24378 | 7/1997 |

OTHER PUBLICATIONS

Kim et al., Uniformity of Current Density Under Stimulating Electrodes, Critical Review in Biomedical Engineering, vol. 17, Issue 6 (1990).

Wiley and Webster, Analysis and Control of the Current Distribution Under Circular Dispersive Electrodes, *IEEE Transaction on Biomedical Engineering*, vol. BME–29, No. 5, May 1982.

Handbook of Pressure Sensitive Adhesives, 2nd Ed., Satax, Ed. (Van Nostrand, NY, 1989).

*Primary Examiner*—Lee Cohen
(74) *Attorney, Agent, or Firm*—Daniel R. Pastirik

(57) ABSTRACT

A universally functional biomedical electrode is disclosed, where the electrode has a resistive element that reduces edge effect by a redistribution of current within the electrode and in mammalian tissue contacting the electrode. In one embodiment, the electrode has at its perimeter in one layer the resistive element that provides a cross-sectional area to reduce edge effect regardless of the type of biomedical instrumentation connected thereto. With the construction of other layers suitable for multifunctional electrode usage, this electrode can serve as a single item in inventory at health facilities.

12 Claims, 8 Drawing Sheets

U.S. PATENT DOCUMENTS

| | | | |
|---|---|---|---|
| 4,166,465 A | 9/1979 | Esty et al. | 128/303.13 |
| 4,269,189 A | 5/1981 | Abraham | 128/303.13 |
| 4,310,509 A | 1/1982 | Berglund et al. | 424/28 |
| 4,323,557 A | 4/1982 | Rosso et al. | 424/28 |
| 4,352,359 A | 10/1982 | Larimore et al. | 128/640 |
| 4,387,714 A | 6/1983 | Geddes et al. | 128/303.13 |
| 4,406,827 A | 9/1983 | Carim | 252/518 |
| 4,458,696 A | 7/1984 | Larimore | 607/152 |
| 4,524,087 A | 6/1985 | Engel | 427/2 |
| 4,539,996 A | 9/1985 | Engel | 128/640 |
| 4,554,924 A | 11/1985 | Engel | 128/640 |
| 4,715,382 A | 12/1987 | Strand | 128/640 |
| 4,732,808 A | 3/1988 | Krampe et al. | 428/355 |
| 4,736,752 A | 4/1988 | Munck et al. | 607/152 |
| 4,846,185 A | 7/1989 | Carim | 128/641 |
| 4,848,348 A | 7/1989 | Craighead | 128/639 |
| 4,848,353 A | 7/1989 | Engel | 128/640 |
| 4,852,571 A | 8/1989 | Gadsby et al. | 128/640 |
| 4,852,585 A | 8/1989 | Heath | |
| 4,871,812 A | 10/1989 | Lucast et al. | 525/186 |
| 4,895,169 A | 1/1990 | Heath | 128/798 |
| 4,917,928 A | 4/1990 | Heinecke | 428/41 |
| 4,917,929 A | 4/1990 | Heinecke | 428/41 |
| RE33,353 E | 9/1990 | Heinecke | 428/40 |
| 4,979,517 A | 12/1990 | Grossman et al. | 607/153 |
| 4,981,903 A | 1/1991 | Garbe et al. | 524/547 |
| 5,009,224 A | 4/1991 | Cole | 128/156 |
| 5,012,810 A | 5/1991 | Strand et al. | 128/640 |
| 5,133,356 A | 7/1992 | Bryan et al. | 128/640 |
| 5,215,087 A | 6/1993 | Anderson et al. | 128/640 |
| 5,225,473 A | 7/1993 | Duan | 524/388 |
| 5,232,838 A | 8/1993 | Nelson et al. | 435/30 |
| 5,270,358 A | 12/1993 | Asmus | 524/55 |
| 5,276,079 A | 1/1994 | Duan et al. | 524/386 |
| 5,330,526 A | 7/1994 | Fincke et al. | 607/142 |
| 5,337,748 A * | 8/1994 | McAdams et al. | 600/396 |
| 5,338,490 A | 8/1994 | Dietz et al. | 252/500 |
| 5,352,315 A | 10/1994 | Carrier et al. | 156/267 |
| 5,354,328 A | 10/1994 | Doan et al. | 607/129 |
| 5,362,420 A | 11/1994 | Itoh et al. | 252/500 |
| 5,385,679 A | 1/1995 | Uy et al. | 252/500 |
| 5,407,717 A | 4/1995 | Lucast et al. | 428/46 |
| RE34,958 E | 5/1995 | Garbe | 424/70.12 |
| 5,438,988 A | 8/1995 | Duan et al. | 128/640 |
| 5,489,624 A | 2/1996 | Kantner et al. | 524/376 |
| 5,506,059 A | 4/1996 | Robbins et al. | 428/457 |
| 5,520,180 A | 5/1996 | Uy et al. | 128/640 |
| 5,571,165 A | 11/1996 | Ferrari | 607/142 |
| 5,674,561 A | 10/1997 | Dietz et al. | 427/208.4 |
| 5,702,753 A | 12/1997 | Yasis | 427/2.12 |
| 5,836,942 A | 11/1998 | Netherly et al. | 606/32 |
| 5,947,961 A | 9/1999 | Netherly et al. | 606/32 |
| 6,019,877 A | 2/2000 | Dupelle et al. | 607/149 |
| 6,044,287 A | 3/2000 | Cornell | 600/391 |
| 6,356,779 B1 * | 3/2002 | Katzenmaier et al. | 600/391 |

* cited by examiner

UNIVERSALLY FUNCTIONAL BIOMEDICAL ELECTRODE

CROSS REFERENCE TO RELATED APPLICATIONS

This application is a divisional of U.S. application Ser. No. 09/326,778, filed Jun. 4, 1999, now U.S. Pat. No. 6,356,779.

FIELD OF INVENTION

This invention relates to a biomedical electrode that can function in each of the following principal uses of biomedical electrodes: electrosurgical, cardiac monitoring, pacing, and defibrillation, and various means of measuring mammalian tissue impedance. As such the biomedical electrode of the present invention is universally functional.

BACKGROUND OF INVENTION

Biomedical electrodes have traditionally been characterized by the type of medical activity that uses them as a transducer at the skin of a mammalian patient, to convert ionically transmitted electrical signals inside the body to electronically transmitted electrical signals outside the body, or to convert electronically transmitted electrical signals outside the body into ionically transmitted electrical signals inside the body.

Electrosurgical generators require a biomedical electrode functioning as a dispersive electrode to recover the electrical signals introduced into the body during surgery. Typical dispersive plate electrodes are disclosed in U.S. Pat. Nos. 4,539,996; 4,387,714; 4,166,465; and 4,269,189.

Cardiac monitoring electrodes, also known as electrocardiography (ECG) electrodes, require a biomedical electrode to detect faint electrical signals emanating from the mammalian heart as a means to monitor the condition of the heart. Such electrodes convert the ionic current in the body to electronic current to be processed by the instrumentation. Typical monitoring electrodes are disclosed in U.S. Pat. Nos. 4,846,185; 5,489,624 and 5,520,180.

While cardiac monitoring electrodes are used to receive electrical signals that originate within a mammalian body, electrosurgical dispersive electrodes, pacing electrodes, and defibrillation electrodes are used to impart and/or receive electrical signals that originate in a piece of external electrical equipment.

Pacing electrodes introduce electrical energy into the mammalian body as a therapy for a weakened, irregular, or slow heart. Typical pacing electrodes are disclosed in U.S. Pat. No. 5,330,526.

Respiration monitoring and cardiac output monitoring electrodes measure transthoracic impedance by passing a current in the microamperes range. Sometimes, the defibrillation/pacing signal is also used to measure impedance.

Defibrillation electrodes introduce a massive, abrupt amount of electrical energy into the mammalian body to induce a correction to the heart in a lifesaving effort to restore proper heartbeat of a heart muscle in ventricular fibrillation. Defibrillation electrodes can also be used in a related application known as cardioversion, whereby a massive, abrupt amount of electrical energy is used to correct persistent irregular heart rhythms, such as atrial fibrillation. In this case it is crucial to synchronize the delivered electrical shock to a specific portion of the repeated ECG signal.

Attempts have been made to create multi-functional electrodes to perform a desired combination of the above activities, typically in some combination of pacing, monitoring, and defibrillation. A mammalian patient who has severe heart or other disease needs monitoring to determine the type and proper amount of heart therapy, including the possibility of pacing a heart over a period of time, or shocking the heart to restore a normal rhythm. Typical multi-functional biomedical electrodes are disclosed in U.S. Pat. No. 4,895,169(Heath); U.S. Pat. No. 5,571,165 (Ferrari); and those electrodes marketed by Cardiotronics of Kimberly Clark Corporation; Katecho; Zoll Medical Devices Corporation; and Meditrace of Tyco Laboratories.

No biomedical electrode has been shown to be able to perform the dispersive electrode function with any of the other three functions especially without adverse effects such as skin damage. But the most significant advance in dispersive electrodes in recent years, as disclosed in U.S. Pat. No. 5,836,942 (Netherly et al.), provides for reduced edge effect using a lossy dielectric material to more evenly distribute the current emerging from the mammalian patient over the entire conductor surface of the dispersive electrode.

SUMMARY OF INVENTION

The art needs a multi-functional electrode that can function in each of the principal ways, i.e., a universally functional electrode. The art needs a universally functional electrode that provides reliable transduction at the skin of a mammalian patient for each of the types of use for biomedical electrodes. The art needs a universally functional electrode that functions individually or in any combination of two, three, four, or five of the types of use for biomedical electrodes.

One aspect of the present invention is a universally functional biomedical electrode, comprising an electrode having a resistive element that reduces edge effect by a redistribution of current within the electrode and in mammalian tissue contacting the electrode.

Another aspect of the present invention is A method of using the electrode, comprising the steps of (a) adhering at least one above-identified electrode to mammalian tissue of a patient; and (b) performing at least one biomedical function selected from the group consisting of monitoring, defibrillation, pacing, electrosurgical dispersing, impedance measuring, and combinations thereof.

A third aspect of the present invention is a biomedical electrode, comprising at least one electronic conductor in contact with an ionically conductive material that interfaces mammalian tissue for exchanging electromagnetic energy, the ionically conductive material containing: (a) at least one highly resistive material, having an impedance that is substantially higher than that of the ionically conductive material; (b) at least one of the said highly resistive material(s) being substantially coplanar with the conductor surface; and (c) the highly resistive material having a geometry, shape and apertures selected to alter the current density profile reaching an interface between the electrode and mammalian tissue.

A feature of the biomedical electrode of the present invention is the ability to both monitor and pace a mammalian heart.

Another feature of the biomedical electrode of the present invention is the ability to both monitor and defibrillate a mammalian heart.

Another feature of the biomedical electrode of the present invention is the ability to both defibrillate and pace a mammalian heart.

Another feature of the biomedical electrode of the present invention is the ability to monitor, pace, and defibrillate a mammalian heart.

Another feature of the biomedical electrode of the present invention is the use of the same biomedical electrode in one instance for electrosurgery and in another instance to both monitor and pace a mammalian heart, even though electrode placement criteria sometimes discourages use of the electrode for all three functions concurrently.

Another feature of the biomedical electrode of the present invention is the use of the same biomedical electrode in one instance for electrosurgery and in another instance to both monitor and defibrillate a mammalian heart, even though electrode placement criteria sometimes discourages use of the electrode for all three functions concurrently.

Another feature of the biomedical electrode of the present invention is the use of the same biomedical electrode in one instance for electrosurgery and in another instance to both defibrillate and pace a mammalian heart, even though electrode placement criteria sometimes discourages use of the electrode for all three functions concurrently.

Another feature of the biomedical electrode of the present invention is the use of the same biomedical electrode in one instance for electrosurgery and in another instance to monitor, pace, and defibrillate a mammalian heart, even though electrode placement criteria sometimes discourages use of the electrode for all functions concurrently.

Another feature of the biomedical electrode of the present invention is the use of the same biomedical electrode in all of the combination of uses cited above and including diagnostic measurements such as dielectric properties of the mammalian tissue.

An advantage of the biomedical electrode of the present invention is the reduction of inventory for medical care facilities by the availability of a single biomedical electrode that can reliably perform all types of biomedical electrode activities identified above.

Another advantage of the biomedical electrode of the present invention is the ability to minimize burns and other tissue damage to skin of a mammalian patient during usage in pacing, defibrillation, and/or electrosurgery.

Another advantage of the biomedical electrode of the present invention is the ability to reduce the extreme discomfort experienced by a mammalian patient during usage of the electrode for external pacing and following cardioversion.

Other features and advantages will become apparent in discussion of the embodiments of the invention in relation to the following drawings.

EMBODIMENTS OF INVENTION

Range of Electrode Operation

The following Table 1 identifies the signal ranges used for each of the types of biomedical electrodes identified above, as is commonly practiced in the various arts of biomedical electrode use.

TABLE 1

| Electrode Type | Frequency of emitted or detected signal | Voltage (V) Voltage encountered by electrode | Current (Amps.) Current passing through electrode. |
|---|---|---|---|
| Monitoring (ECG) | 0–1 kHz | $0–3 \times 10^{-3}$ | $0–<10^{-6}$ |
| Defibrillation | 0–15 Hz | 0–3000 | 0–100 |
| Pacing | 0–1 kHz | 0–300 | $0–200 \times 10^{-3}$ |
| Electrosurgical Dispersive | 358 kHz–3 MHz | 0–12,500 | 0–2 |
| Impedance (Plethysmography) | 1 kHz–1 MHz | 0–10 | $1 \times 10^{-6}–1 \times 10^{-3}$ |

As can be seen from Table 1, there is very little in common among the five types of biomedical electrodes. To construct a biomedical electrode of the present invention, one must take into account each of the ranges to achieve reliable and safe performance.

Figure 1:
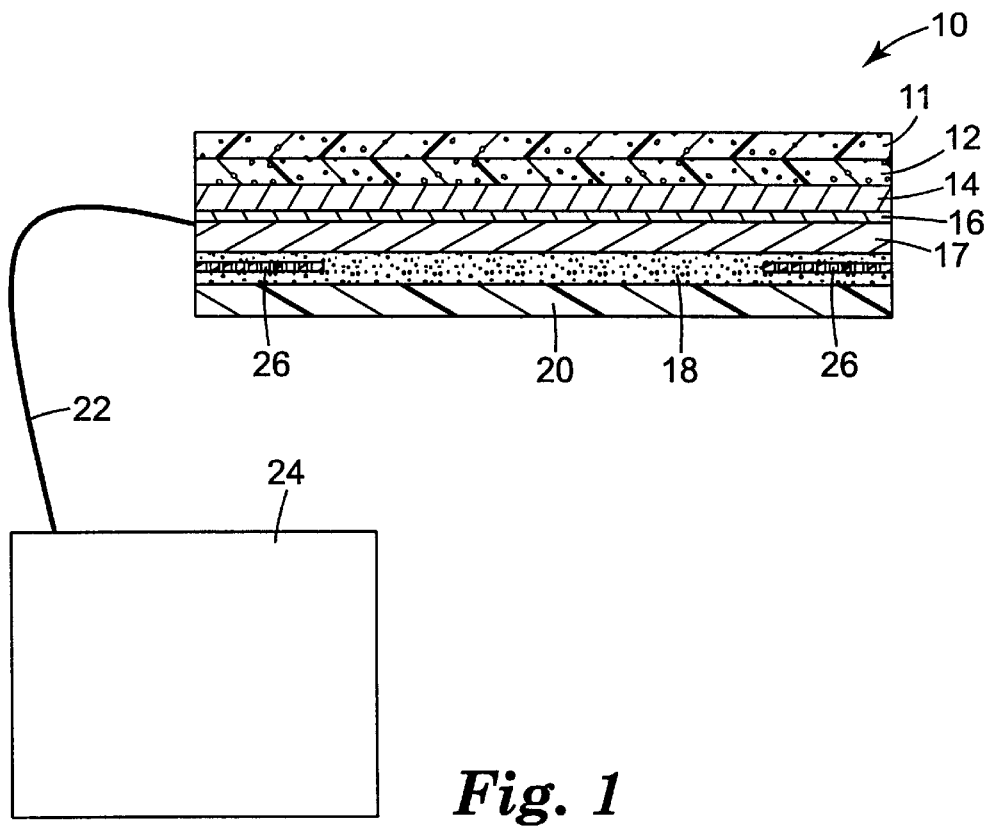
FIG. 1 is a cross-sectional view of one embodiment of the biomedical electrode of the present invention.

FIG. 1 shows a cross-sectional view of one embodiment of the present invention that has required and optional components. Electrode 10 has several layers. When viewed from the outermost layer from skin of a patient, the electrode 10 has a first electrically insulative backing layer 11, optionally a second electrically insulative backing layer 12, a galvanically active, electronically active conductor layer 14, a galvanically inactive, electronically active conductor layer 16, optionally a galvanically active, electronically active conductor layer 17, and a layer of ionically conductive adhesive 18. To protect the layer 18 of conductive adhesive until use, optionally, a release liner 20 is used.

Backing Layer

Materials useful for the backings 11 and 12 are well known and commercially available. Nonlimiting examples of such backing materials include polyester films, polyolefin films, and the like.

Electrically non-conductive backings 11 and 12 preferably are very conformable to the various contours of the mammalian body. Many materials can be used for this purpose, as will be apparent to those skilled in the art. In one presently preferred embodiment, a closed-cell foam is considered particularly suitable. One such material is commercially available as Volara brand foam from Voltek, Inc. of Massachusetts. Another is commercially available as a laminate of nonwoven polypropylene and low density polyethylene backing from Milliken of Spartanburg, S.C.

The electrically non-conductive backing 11 can have a thickness ranging from about 0.25 mm (0.01 inch) to about 1.5 mm (0.06 inch). The second electrically insulative layer 12 generally is a plastic sheet such as polyester, typically 0.025 mm to 0.127 mm thick. Optional layer 12 is used as the base layer onto which the first electronically conductive layer 14 is attached.

Galvanically Active, Electronically Active Conductor Layer

Materials useful for the layer 14 are well known and commercially available. Nonlimiting examples of such galvanically active, electronically active materials include silver metal, tin metal, alloys of tin and lead, and the like, whether prepared as a foil, in an ink, or vapor-deposited according to U.S. Pat. No. 5,506,059 (Robbins et al.), the disclosure of which is incorporated herein by reference. Presently preferred is an ink of silver commercially available as "R301S" ink from Ercon, Inc. of Wareham, Mass., USA.

Layer 14 can have a thickness ranging from about 0.00127 mm (0.05 mil) to about 0.127 mm (5 mils) and preferably from about 0.00254(0.1 mils) to about 0.0254 mm (1 mil) when deposited as an ink. There may be one location on layer 14, that has a wire 22, that connects electrode 10 to biomedical instrumentation of choice (generally 24).

Galvanically Inactive, Electronically Active Conductor Layer

Materials useful for the layer 16 are well known and commercially available. As used in this invention, the term "galvanically inactive" is a relative term in that it means a material that is less galvanically active than the galvanically active material used for layer 14. For example, steel alloys are generally less galvanically active than silver or tin even though they possess some galvanic activity. Such relative galvanic activity is a function of both the position of the metal or alloy in the electrochemical series with respect to each other and also depends on the electrolyte in which the galvanic activity is likely to occur. Typically for the purposes of this example, one material is galvanically more active than another if a galvanic cell is formed between them in the presence of the salt electrolyte of the conductive adhesive and if the first material has a negative potential with respect to the second material. Nonlimiting examples of such galvanically inactive, electronically active materials include graphite, platinum and certain metal alloys, whether prepared as a foil or deposited as an ink.

Layer 16 can have a thickness ranging from about 0.0127 mm (0.05 mils) to about 0.127 mm (5 mils) and preferably from about 0.025 mm (1 mils) to about 0.075 mm (3 mils). Presently preferred for layer 16 is a graphite ink (Acheson SS 24636, available from Acheson Colloids Co. of Port Huron, Mich.) printed on the layer 14.

Galvanically Active, Electronically Conductive Layer

Materials useful for the layer 17 are well known and commercially available. Nonlimiting examples of such galvanically active, electronically active materials include silver metal, tin metal, alloys of tin and lead, and the like, whether prepared as a foil, in an ink, or vapor-deposited according to U.S. Pat. No. 5,506,059 (Robbins et al.), the disclosure of which is incorporated herein by reference. Presently preferred are inks of silver/silver chloride which contains equimolar parts of silver and silver chloride or which is commercially available as "R301" ink from Ercon, Inc. of Wareham, Mass., USA.

Layer 17 can have a thickness ranging from about 0.00127 mm (0.05 mil) to about 0.127 mm (5 mils) and preferably from about 0.00254(0.1 mils) to about 0.0254 mm (1 mil) when deposited as an ink.

Ionically Conductive Adhesive

Ionically conductive adhesives useful for the layer 18 are well known and commercially available or described in the literature. Generally such adhesives identified as ionically conductive are described in the *Handbook of Pressure Sensitive Adhesives*, 2nd Ed., Satas, Ed., (Van Nostrand, N.Y. 1989). Nonlimiting examples of ionically conductive adhesives are those adhesives disclosed in U.S. Pat. Nos. 4,524,087; 4,848,353; 5,674,561; 5,438,988, the disclosures of which are incorporated by reference herein. Commercially available ionically conductive adhesives are available from Ludlow under the brand Promeon™.

The thickness of adhesive layer 18 can range from about 0.127 mm (5 mils) to about 2.54 mm (100 mils) and preferably from about 0.635 mm (25 mils) to about 1.397 mm (55 mils).

Thus, the total thickness of electrode 10 can range from about 1.02 mm (40 mils) to about 3.56 mm (140 mils) and preferably from about 1.5 mm (60 mils) to about 2.03 mm (80 mils). At this thickness, electrode 10 is a low profile, flexible, and durable product for long term placement for the activities of monitoring, pacing, defibrillation, and electrosurgery.

Optionally, to assist releasably securing the electrode 10 to the mammalian patient, one can use a border of pressure sensitive adhesive, preferably hydrophilic, beyond the perimeter of operational components of the electrode. Moreover, the ionically conductive adhesive that is an operational component of the electrode is preferably hydrophilic. The hydrophilic adhesives useful in the present invention should be biocompatible with mammalian skin and can be formulated in both ionically conductive and non-conductive embodiments. The ionically conductive adhesives are useful in contact with both mammalian skin and conductor plates 14 and 17. The non-conductive adhesives can be used beyond the perimeter of the conductor plates 14 and 17.

Preferably, if the expense of a single field 32 of hydrophilic, ionically conductive, biocompatible, pressure sensitive adhesive is not greater than the expense during manufacturing of applying two different types of adhesive to comprise field 32, then a single field is used even if ionic conductivity is not required to be present in the perimeter section of field 32 not contacting conductor plates 14 and 17.

Nonlimiting examples of hydrophilic adhesives useful in connection with the present invention include those compositions disclosed in U.S. Pat. No. 4,524,087 (Engel); U.S. Pat. No. 4,539,996 (Engel); U.S. Pat No. 4,848,353 (Engel) and U.S. Pat. No. 5,133,356 (Bryan et al.); U.S. Pat. No. 5,225,473 (Duan); U.S. Pat. No. 5,276,079 (Duan et al.); U.S. Pat. No. 5,338,490 (Dietz et al.); U.S. Pat. No. 5,362,420 (Itoh et al.); U.S. Pat. No. 5,385,679 (Uy et al.); copending and coassigned applications PCT Publication Nos. WO 95/20634 and WO 94/12585; and PCT Patent Application Publication Nos. WO97/24378; WO97/24376; and WO97/24149, the disclosures of which are incorporated by reference herein. Further nonlimiting examples of adhesives that do not have ionically conductive properties but would be useful beyond the perimeter of operational components of the electrode 10 include U.S. Pat. Nos. 4,871,812 and 5,407,717 (both Lucast et al.); U.S. Pat. No. 4,981,903 and Re 34,958 (both Garbe et al.); U.S. Pat. No. 5,009,224 (Cole); U.S. Pat. No. 5,232,838 (Nelson et al.); and U.S. Pat. No. 5,270,358 (Asmus); PCT Publication WO 95/27016; and adhesives commercially available from the Medical Specialties Department of 3M Health Care, 3M Company, St. Paul, Minn., the disclosures of all of which are incorporated herein by reference.

In some embodiments, adhesive can be used for holding other components of the electrode 10 together. Nonlimiting examples of suitable adhesives include acrylate ester adhesives, and more particularly acrylate ester copolymer adhesives. Such adhesives are generally described in U.S. Pat. No. 2,973,286; Re 24,906; Re 33,353; U.S. Pat Nos. 3,389,827; 4,112,213; 4,310,509; 4,323,557; 4,732,808; 4,917,928; 4,917,929; and European Patent Publication 0 051 935, all incorporated herein by reference.

Release Liner

Release liner 20 can be any construction suitable for protecting the conductive adhesive 18 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Transducer Current Redistribution Component

One aspect of the present invention is the discovery of the necessity to cause redistribution of current within mammalian tissue in the vicinity of, or directly contacting, electrode 10. While mammalian tissue is capable of exchanging electromagnetic energy with electrode 10 under conventional multifunctional electrodes, the current density profile of electrode 10 unexpectedly and significantly diminishes the edge effect of electrode 10, for those uses of electrode 10 where high energy is apt to damage the mammalian tissue contacting electrode 10 at such edges or cause considerable pain for the patient.

Reduction of edge effect has been an advantage of the Netherly dispersive electrode disclosed in U.S. Pat. No. 5,836,942 (Netherly et al.). But the edge effect reduction of Netherly et al. is based on the alteration of impedance of the conductor surface.

The redistribution of current in mammalian tissue according to the present invention operates on a principle concerning the inhomogeneity of the resistance of the total area of the interface between the tissue and the electrode to exchange electromagnetic energy with the mammalian tissue of the patient.

There are at least three embodiments for the purpose of reducing edge effect in a manner that cause a redistribution of current density within the mammalian tissue:

(1) limiting the resistance (preferably by limiting the cross-sectional area) of conduction through the conductive adhesive with a highly resistive material which modifies the z-axis impedance of the adhesive system of the electrode as a gradient from the center toward the periphery (Peripheral Z-Axis Adhesive Screen);

(2) limiting the cross-sectional area of the conductor surface by selectively blocking conduction with a highly resistive material (Peripheral Z-Axis Conductor Screen); and (3) limiting the cross-sectional area of the conductor surface in the X-Y plane via printing or other contacting of the conductive material from the center outwards towards the perimeter of the electrode (X-Y Plane Gradient Conductor Surface).

Optionally with one of the above three embodiments, one can also extend the hydrophilic conductive adhesive contact with the mammalian tissue beyond the perimeter of contact of that adhesive with the conductor (Hydrophilic Ionically Conductive Border Adhesive).

In each of these embodiments, the current density at the edge of the conductor (or at the contour of the contact between the conductor and the ionically conductive adhesive) is altered by spreading its effect to a wider surface area than a line constituting the edge between electronically conductive and insulative areas of the electrode 10. As reported in the literature (Kim et al, "Uniformity of current density under stimulating electrodes", Critical Reviews in Biomedical Engineering, Volume 17, Issue 6 (1990) and in Netherly et al., the edge of a conductive surface receives a disproportionate amount of electromagnetic energy, and the mammalian tissue contacting that edge also receives that disproportionate amount. In high energy pacing, defibrillation, cardioversion, and dispersive electrosurgical procedures, the patient can experience excruciating pain at such edges, resulting in electrical burns and considerable tissue damage.

Each of the three embodiments and optional addition will be discussed in greater detail, in the order recited above.

Peripheral Z-Axis Adhesive Screen

Embedded within ionically conductive adhesive is a physical screen to the conduction of current between skin of a mammalian patient and medical instrumentation, regardless of the direction of conduction. As seen in FIG. 1, a thin layer of a z-axis barrier screen 26 is seen embedded at the periphery of the adhesive layer 18. Alternatively, the screen can have the same size in the x-y plane as the conductive adhesive depending on the pattern of the porosity of the screen.

The properties of the screen 26 are significant to the performance of the electrode 10 as a universally functional electrode to meet the ranges seen in Table 1 above. Specifically, those properties are previously unknown for the performance of biomedical electrodes in this configuration.

One property of screen 26 is its partial physical or mechanical barrier to the conduction of current in the z-axis of the electrode, shown by arrows Z—Z in FIG. 1. The barrier inhibits but does not prevent the conduction of current between skin of a patient and medical instrumentation 24.

This physical inhibition is unlike the lossy dielectric properties of the Netherly Plate Electrodes as disclosed in U.S. Pat. No. 5,836,942 (Netherly et al.) because the lossy dielectric material operates in an electrical regime whereas screen 26 operates in a physical or mechanical regime. The screen 26 is highly resistive except for those places where it is not at all.

Screen 26, as the term implies, is not a solid film but rather has holes extended from its one major surface to its other major surface. Representative examples of screens range from woven scrims with a massive proportion of scrim area comprising holes to a membrane that is through-porous in a tortuous manner with a very small proportion of the membrane comprising holes. Another nonlimiting example of a screen that has utility is one where the limitation of cross sectional conduction area is accomplished by a single large hole, or group of holes, which employ a complex border geometry to limit the area of the hole(s). In other words, in this case the limitation of cross sectional conduction area is physically accomplished by a convoluted but continuous hole extending through the screen, rather than a series of discrete holes whose edges are separate and not intersecting.

Physically, a screen 26 comprising of a series of small, discrete holes can be characterized based on the size of the pores, the geometric shape of the pores (round, square, elliptical, etc.), the Z-axis length of the pores, the spacing distance among the pores, and the spacing pattern among the pores. This pattern may be either a regularly repeated pattern (orthogonal, trigonal, hexagonal, etc.), or an irregularly repeated pattern, or an essentially random pattern of holes. In general, however, a goal of the manipulation of these several variables is to substantially reduce the cross-sectional area of the screen, for the purpose of increasing the Z-axis impedance of the conductive medium in which the screen is embedded.

The pore diameter of screen 26 can range from about 0.03 mm to about 1.27 mm and preferably from about 0.10 mm to about 0.75 mm.

When combined with a specific pore size, the spacing of the pores should be such as to achieve a percentage of the surface area of pores or holes in the screen 26 which can range from about 1% to about 30% and preferably from about 3% to about 20%.

The thickness of screen 26 can range from about 0.020 mm to about 1.000 mm and preferably from about 0.050 mm to about 0.250 mm.

Preferably, another property of screen 26 comprising of a series of small, discrete holes is its gradient in hole size and/or spacing from the periphery region of electrode 10 toward the center of the electrode 10. Such a gradient increases z-axis electrical conduction (or reduces electrical barrier properties, depending on one's perspective) gradually or in pre-determined steps from the outer edge throughout the periphery region and toward the center of the electrode 10. Thus, the useful ranges of physical properties of the screen 26 identified above, e.g., percent surface area of pores, can be controlled to provide a gradual or stepwise transition from a higher screening of z-axis electrical conduction at the edge of the electrode 10 to a lower or absence of screening of z-axis electrical conduction at the center of the electrode.

Physically, a screen 26 comprising a small number of holes with a complex or convoluted border geometry can be characterized by its geometric shape and the reduction of cross sectional area of conduction. Nonlimiting examples include graphical shapes such as sunbursts with very long and thin points, or radial spokes extending from a central hub like the spokes on a wheel.

In the area of the geometric shape that is intended to provide a substantial reduction in cross sectional conduction area, (i.e., just the rays of the sunburst, or just the spokes of a wheel) the percentage of the surface area of the rays or spokes in the screen 26 can range from about 1% to about 30%, and preferably from about 3% to 20%.

The thickness of screen 26 can range from about 0.020 mm to about 1.000 mm, and preferably from about 0.050 mm to about 0.250 mm.

Preferably, another property of screen 26 comprising a small number of holes with a complex or convoluted border geometry is its gradient in width and/or radial dispersion of the convoluted geometry from the center of the electrode outwards towards the periphery of the conductive adhesive. With a sunburst geometric shape this could involve a tapering and/or a sinusoidal variation in the direction of the individual rays as they extended out from the center of the screen. With a spoked wheel geometric shape, this could involve a tapering and/or a branching of the spokes to form a fractal image extending out from the central hub of the design.

The percentage area of adhesive layer 18 having some level of z-axis conductor screening can range from about 2% to about 60% and preferably from about 5% to about 45%.

Materials for screen 26 are available to those skilled in the art. Nonlimiting examples of such materials include the non-conductive sheet material comprising the backing of Transpore™ tape sold by 3M Co. of St. Paul Minn., plastic sheets with a pattern of holes such as door/window screens made from highly resistive materials, and the like. Another nonlimiting example would include the use of a non-woven scrim material upon which is printed a screen pattern using a highly resistive ink. The percentage of the Z-axis screening can be formed using any substantially occlusive printing pattern in a manner as known to those in the printing industry. Nonlimiting examples of such patterns would include an exact printed replica of a physical screen where the pores are defined by the absence of the highly resistive ink, or a halftone pattern, or an essentially random pattern of ink dots such as are applied to a substrate by an inkjet or laser printing process. It can be appreciated that this example would have particular utility in producing a screen consisting of a small number of holes with a complex or convoluted border geometry, and by this method extremely complex border patterns could be easily, cheaply, and reproducibly created, such as by use of printing techniques including without limitation, electrographic printing, lithographic printing, inkjet printing, thermal mass transfer printing, laser printing, and the like.

Peripheral Z-Axis Conductor Screen

Figure 2:
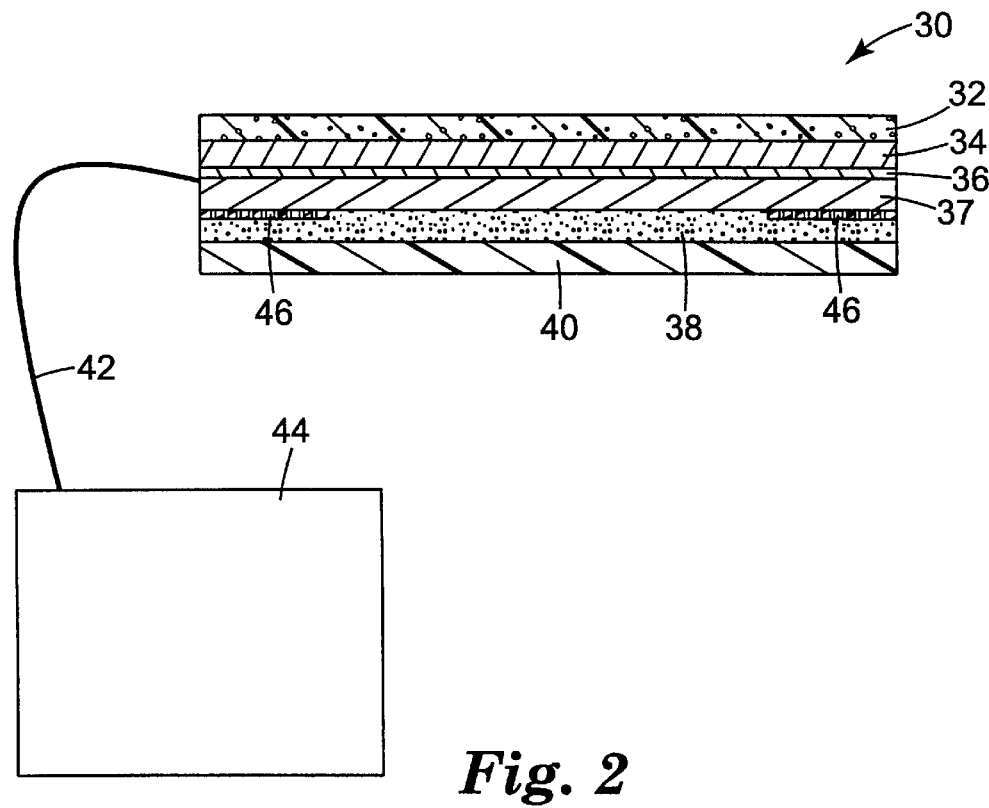
FIG. 2. is a cross-sectional view of a second embodiment of the present invention.

FIG. 2 shows an electrode 30 that is very much similar to electrode 10 with an insulative backing layer 32, a galvanically active, electronically conductive layer 34, a galvanically inactive, electronically conductive layer 36, a galvanically active, electronically conductive layer 37 and an ionically conductive adhesive layer 38 (with liner 40) except that screen 46 is located in, or on a major surface of, galvanically active, electronically active conductor layer 37 contacting ionically conductive adhesive layer 38. The same materials can be used for each of layers 32, 34, 36, 37, 38, 40, and for wire 42, and instrumentation 44.

Screen 46 can be made from any of the materials used for screen 26 but preferably is printed as highly resistive or electronically insulating ink onto the major surface of layer 37 contacting layer 38. Because screen 46 need not be a physically separate component such as screen 26 is, the percentage area of z-axis screening can be formed using any substantially occlusive printing pattern of half tones or continuous tones in a manner as known to those in the printing industry. Nonlimiting examples of such patterns would include an exact printed replica of a physical screen where the pores are defined by the absence of the highly resistive ink, or a halftone pattern, or an essentially random pattern of ink dots such as are applied to a substrate by an inkjet or laser printing process. Additionally, it would be possible to create a screen pattern consisting of a small number of holes with a complex or convoluted border geometry by this printing process. The screen 46 should be constructed to achieve a percentage of the surface area of pores, holes, or ink voids which can range from about 0.2% to about 30%, and preferable from about 1% to about 15%.

The percentage area of conductor layer 37 having some level of z-axis conductor screening can range from about 2% to about 60%, and preferably from about 5% to about 45%.

X-Y Plane Gradient Conductor Surface

This embodiment also concerns the conductor but differs from the Peripheral Z-Axis Conductor Screen 46 in that the conductive material itself, e.g., ink, is printed or otherwise arrayed in a manner that is graphically like the printing of a sunburst design, or spokes on a wheel design of screen 46. This embodiment is completely distinct from the others, however, in that the reduction of cross sectional conductor area occurs within the conductive layers themselves, rather than at some point on the surface of the conductor or in an adhesive layer above the conductor. This is accomplished by the printing or otherwise arraying the conductive layers so that they originate from a central location and extend outward by means of many rays, spokes, and/or branches towards the periphery of the conductor element. In this embodiment, the reduction of the cross sectional conductor area occurs entirely in the X-Y plane of the conductor. The cross sectional area of the conductor is defined by the width and thickness of the individual rays, spokes, or branches of conductive material at any point on the conductor surface. As these individual branches extend from a central location, their cross sectional area may be reduced by reducing the width and/or thickness of the individual ray, spoke, or branch elements. This approach would have particular utility if the conductor surface were constructed by the printing of a conductive ink, and if the ink were applied in multiple layers both the width and thickness of the resulting conductor pattern could be controlled. This reduction of the cross sectional area of the conductor itself in the two-dimensional X-Y plane is entirely analogous to the structure of a tree in a three dimensional space, and in the case of the tree there is a central point (the trunk) from which extend many branches which repeatedly separate out into smaller and smaller limbs and twigs until the outer "edge" of the tree is reached. In the case of the tree, the sap in the trunk flows upward through the trunk and progressively moves through smaller and smaller branches until it finally reaches the end of each twig and passes into the leaf structure. In the case of an X-Y plane gradient conductor surface, the electrical energy flows from the central location out through individual rays, spokes, or branches which continue to narrow in width and/or thickness until the end of an individual pathway is reached, and at that point the electrical energy leaves the conductor and flows into the layer 38 of ionically conductive adhesive above it. This progressive narrowing of the conductor pathway is what accomplishes the increase in impedance necessary to reduce the edge effect of the electrode in this embodiment, and by so doing, the current is redistributed in the mammalian tissues to which the electrode is affixed.

It can be appreciated that by the use of printing the conductor with conductive inks, this embodiment affords and extremely elegant and simple method of accomplishing a reduction of cross sectional conductor area with a built-in gradient to it, so that the current in the mammalian tissue may be smoothly redistributed, rather than in abrupt steps or levels which may otherwise produce secondary zones of increased current density or edge effect. In addition, the use of printing technology allows an extremely high level of conductor branching and narrowing to be achieved, and in this embodiment a fractal branching design would have particular utility to smoothly distribute the current in mammalian tissue. The same printing techniques as described above can be used for this embodiment as well.

Optional Hydrophilic Ionically Conductive Border Adhesive

There are advantages to having an hydrophilic adhesive, preferably ionically conductive, contacting the mammalian tissue in a contact area that is larger than the perimeter of contact between the ionically conductive adhesive and the conductor system. One advantage, which is discussed at length by Kim et al., ("Uniformity of current density under stimulating electrodes", *Critical Reviews in Biomedical Engineering*, Volume 17, Issue 6, 1990 the disclosure of which is incorporated by reference herein) suggests that the ionically conductive adhesive surface area interfacing with the mammalian tissue permits resistive x-y plane electromagnetic energy transport through the adhesive before contacting the perimeter of the conductor. This resistive, lateral energy transport route reduces the concentration of current in the mammalian tissue at the periphery of the conductor.

As explained in PCT Patent Publication WO 97/43007 and U.S. Pat. No. 5,947,961 (Netherly et al.) the disclosure of which is incorporated herein, however, there is an unexpected additional benefit of having a hydrophilic adhesive in contact with the mammalian tissue over an area that extends beyond the periphery of the conductor. A hydrophilic adhesive which extends beyond a lossy dielectric conductor element can work with that lossy dielectric conductor element to further reduce the concentration of current in mammalian tissue by the partial desiccation of the epidermis by the hydrophilic adhesive layer. This desiccation of the mammalian epidermis increases the impedance in the epidermis, and as a result the concentration of current in the layers of mammalian tissue below the epidermis is reduced. The distance by which the conductive adhesive can extend beyond the conductor can range from about 2 mm to about 25 mm, and preferably from about 4 mm to 18 mm.

Method of Making Electrodes

Electrode 10 can be made using conventional tab/pad style or dispersive plate style electrodes as described in U.S. Pat. No. 4,352,359 (Larimore); U.S. Pat. No. 4,524,087 (Engel); U.S. Pat. No. 4,539,996 (Engel); U.S. Pat. No. 4,554,924 (Engel); U.S. Pat. No. 4,848,348 (Carim); U.S. Pat. No. 4,848,353 (Engel); U.S. Pat. No. 5,012,810 (Strand et al.); U.S. Pat. No. 5,133,356 (Bryan et al.); U.S. Pat. No. 5,215,087 (Anderson et al.); and U.S. Pat. No. 5,276,079 (Duan et al.), the disclosures of which are incorporated by reference herein. Generally, multiple layered electrode 10 can be assembled from rolls of starting materials for insulative electronically non-conductive backing 12, upon which is applied conductor layers 14, 16, and 17, upon which is placed screen 26 at the periphery, upon which is coated an uncured field 18 of hydrophilic, ionically conductive pressure sensitive adhesive. Alternatively, a cured field 18 of adhesive having screen 26 placed therein can be laminated at that step in the process. The analogous arrangement of layers for electrode 30 is used, except that screen 46 is applied to layer 37 before coated or cured field 38 of adhesive is placed.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. No. 4,715,382 (Strand); U.S. Pat. No. 5,133,356 (Bryan et al.); and copending, coassigned U.S. Pat. No. 5,702,753 (Yasis et al.), the disclosures of which are incorporated by reference herein, and U.S. Pat. No. 5,352,315 (Carrier et al.).

Whether the embodiment of FIG. 1 or the embodiment of FIG. 2, the organization of layers of electrode 10 or 30 provides for a universally functional biomedical electrode. The combination of the galvanically active layers 14 and 34 with the galvanically inactive layers 16 and 36, respectively, benefit from the properties disclosed in U.S. Pat. No. 3,976,055 (Monter) and U.S. Pat. No. 4,852,571 (Gadsby). Moreover, any deterioration of either of layers 14 or 34 or layers 16 or 36 during use of electrodes 10 or 30, respectively, is compensated by the durability of the other of those layers. For example, any deterioration of layer 14 or 34 during pacing is compensated by the durability of layer 16 or 36 because a galvanically inactive conductor is not affected by the performance criteria associated with pacing. Also, any deterioration of layer 17 or 37 during monitoring or defibrillation is compensated by the durability of layer 16 or 36 because a galvanically inactive conductor is not affected by the performance criteria associated with monitoring or defibrillation. Also the galvanically inactive layer 16 or 36 does not change its bulk conductivity as a result of the performance criteria associated with monitoring or defibrillation, and therefore protects the more susceptible galvanically active layer 14 or 34 underneath. This allows the layers 14, 34 to spread the electrical current in the X-Y direction so that current may pass through the layers 16, 17 and 36, 37 in the Z direction to the skin of the subject even if the layer 17, 37 has deteriorated or its conduction of current in the X-Y direction is compromised due to excessive passage of current from defibrillation of pacing.

Figure 3:
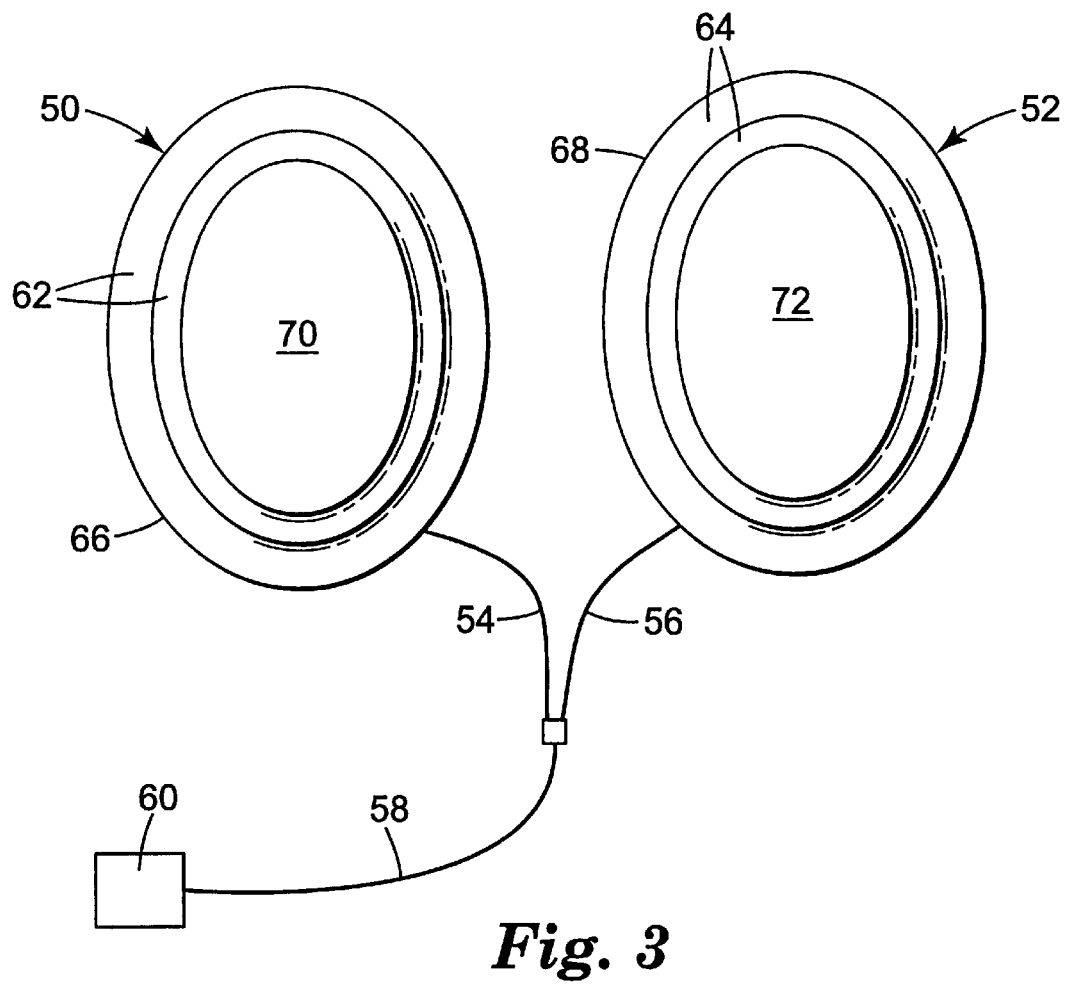
FIG. 3 is a perspective view of a pair of biomedical electrodes of the present invention useful for a combination of monitoring, pacing, and defibrillation.

Electrodes can be used singly or multiply according to the particular desired usage with medical instrumentation. FIG. 3 shows a pair of electrodes 50, 52 electrically connected by wires 54, 56 to a common lead wire 58 for assured proper electrical and mechanical connection at plug 60 to medical instrumentation of the proper kind. Although not normally seen in either electrode 10 or 30, screens 62, 64 are shown for purposes of illustration only to give a sense of perspective of the relative conductive surface areas of electrodes treated by screens 62 and 64 in some fashion. Further, FIG. 3 shows the relative step-wise gradient of screens 62 and 64 to illustrate the manner of decreasing gradient as the screen proceeds from outer edge 66, 68 to the center 70, 72 of electrodes 50, 52.

In those circumstances where the electrodes 50, 52 are intended to function as a pair and in a manner where specific placement on skin of a mammalian patient is critical to performance of the electrode, e.g., when placing pacing electrode pairs, one can alter the construction of each electrode 50 and 52 to accommodate the specificity of the electrodes in their respective placement. For example, the pair of electrodes are configured such that electrode 50 is designated for placement at the apex of the chest to have negative polarity, whereas electrode 52 is designated for use as positive polarity. With such specificity, electrodes 50 and 52 can be optimized to provide the best possible conductor layers for negative polarity and positive polarity, respectively. Optimization of electrodes 50 and 52 could be arranged in terms of ratio of silver to silver chloride, pH, buffers, salts, and the like to optimize one electrode as a cathode for negative polarity and an anode for positive polarity.

Another method of optimization is to reduce the "edge effect" between the proximal edges of the pair of electrodes applied as in the anterior-apex position on the chest. In this case, the screen patterns of 26, 46 are asymmetrical and designed to provide a uniform current distribution in the mammalian tissue under each electrode.

Usefulness of the Invention

The selection of either electrode 10 or electrode 30 to be used singly or multiply or the selection of electrodes 50, 52 connected as a pair depends on the particular medical care to be performed on the mammalian patient. Sizes of such electrodes 10, 30, 50, and 52 can be varied to accommodate various sizes of patients from premature infants to large adults and to accommodate various locations of placement on mammalian skin.

Tests within protocols established by the Association for Advancement of Medical Instrumentation (AAMI) prove that such electrodes of the present invention can perform reliably within the ranges shown in Table 1. Combined with preferred materials for backing layer, conductive layers, and conductive adhesive layer, one skilled in the art can now construct a universally functional biomedical electrode. The use of a universally functional biomedical electrode limits the number of inventory products that a medical care facility needs to store without any diminution of any medical service quality.

Without being limited to a particular theory, the two embodiments of FIGS. 1 and 2 involve the use of Z-axis impedance in the conductive adhesive and conductor, respectively. It should be noted that this is a special case of Z-axis impedance, and while prior art exists in the literature for the imposition of "resistive means" [(Wiley and Webster, "Analysis and Control of the Current Distribution under Circular Dispersive Electrodes, *IEEE transactions on Biomedical Engineering*, Vol. BME-29, No. 5, May 1982) and (Kim et al, "Uniformity of current density under stimulating electrodes", *Critical Reviews in Biomedical Engineering*, Volume 17, Issue 6, 1990) the disclosures of which are incorporated by reference herein] upon either the conductor or in the adhesive that will act in the Z-axis, in this case the "resistive means" themselves form the basis of a rather peculiar paradox. To state the case most succinctly, these "resistive means" are unique in that they do not physically exist, and it is their lack of existence that makes them both novel and useful. The best way to explain this contradiction is to actually describe the working of normal resistive means first, and then contrast this with the "resistive non-means" of the screen 26, or the screen 46, or the X-Y Plane Gradient Conductor pattern of layers 14, 16, and 17.

The characterization of the conductive properties of materials is a well developed and exact science, and there are several ways to quantify the conductive properties of materials. For the sake of this discussion, the conductivity of a material will be defined in terms of its ability to resist the flow of electricity, using the unit of measurement known as the Ohm. In general this resistance to the flow of electricity is defined as the vector quantity impedance, which is made up of the scalar quantities resistance and reactance. A full discussion of this particular subject is contained in the U.S. Pat. No. 5,836,942 (Netherly et al), and is incorporated herein by reference.

To momentarily move to the larger scope of the current passing through multifunctional (MFE) electrodes (generally the functions shown in Table 1, except for dispersive electrodes), it has been shown that while the defibrillation current does constitute a time-dependent waveform, it is either a single half-wave (monophasic) or single full wave (biphasic) shape which is essentially a massive surge of direct current. While the currents used for the pacing and ECG measurement functions can be categorized by some regular amplitude characteristics, as seen in Table 1 above, the frequencies in all cases are very low and for all intents and purposes behave like direct current. It has been experimentally shown that the range of parameters disclosed in U.S. Pat. No. 5,836,942 (Netherly et al.) have far too high an impedance to pass current in the MFE realm. While it has been shown that the lossy dielectric properties of the materials disclosed in Netherly et al can be substantially altered to become more lossy (more resistance and less reactance), if it is the case that highly lossy dielectric means could be used in multifunctional electrodes, it is almost certain that the range of useful parameters would be located in an almost totally resistive regime.

To control current in an MFE electrode, current distribution will be changed by adjusting the scalar quantity resistance alone, so that in all cases the impedance and resistance will always be substantially identical in magnitude. In other words, the use of the term "resistive means" in this discussion of one theory is technically and literally accurate with the following caveat: conductive adhesives are generally composed of large polar molecules and can show a phase angle that is not strictly attributable to a purely resistive element, especially at frequencies used by ESU generators.

Except in the case of superconductivity, all conducting materials have a finite resistance, meaning that in all cases, materials do not pass electricity with perfect efficiency. This efficiency is directly proportional to the material's resistance in Ohms, and so the silver layer in an ECG or MFE electrode will be very efficient in conducting electricity, with an impedance typically on the order of 0.01 Ohms. To reduce the current flow at the edge of a biomedical electrode, the resistance at the outer edge must be substantially higher than at the center, and this is fully defined in Wiley and Webster's publication cited above. Various means for doing this are suggested by Webster in later publications, and also by Kim and Kim et al in other publications, and in all cases involve the positioning of highly resistive materials (carbon filled plastics, etc.) between the conductor of the electrode and the skin of the patient. Similarly, Kim's suggestion of using concentric rings of conductive adhesive of various resistances would be a similar solution to the problem. In all cases, the concept embodied is the physical addition (or imposition) of materials with higher resistance near the edge of the electrode (or increase the resistance of the adhesive materials already present), so as to limit the flow of electricity to that location.

While the resistance of a homogenous material is a constant and isotropic property, meaning that it is the same in all locations and in all directions, the total resistance of the selfsame material is inversely proportional to the total volume of the material carrying the electricity. This behavior is mathematically expressed in the $$\frac{1}{R_{Total}} = \frac{1}{R_1} + \frac{1}{R_2} + \frac{1}{R_3} + \ldots + \frac{1}{R_n}$$

equation for sum of parallel resistances:

So for a conductor of a fixed length and diameter with a resistance of 5 Ohms, the resistance of two of these conductors acting in parallel would be:

$$\frac{1}{1/5 + 1/5} = \frac{1}{2/5} = \frac{1}{.4} = 2.5 \text{ ohms}$$

Similarly, for the resistance of four of the same conductors acting in parallel, one would have:

$$\frac{1}{1/5 + 1/5 + 1/5 + 1/5} = \frac{1}{4/5} = \frac{1}{.8} = 1.25 \text{ ohms}$$

For parallel resistances that are all the same value, one can see that the relationship between the number of conductors and the total resistance is in exact inverse proportion, with the resistance being halved as the number of conductors is doubled, and vice versa. While one usually visualizes this situation as a number of discrete 1 Ohm resistors with their common ends soldered together, in actual fact this relationship also holds for wires of different diameters. In particular, since the resistive material in question is homogenous, the relevant quantity that has an inverse relationship with the total resistance of the material is its cross sectional area. In theory, at least, it is possible to create a resistor of any desired value out of a copper wire of fixed length by specifying the diameter (or cross sectional area) of the wire to some arbitrarily small dimension.

It should be noted that the intrinsic resistivity of copper is different than aluminum. Therefore, for the same dimensions, the copper and aluminum wire of the same length would have different resistances.

Note especially that the length of the wire does not enter into this relationship, as long as it is constant, and with certain dimensions a "wire" may be specified which has relevance to large biomedical electrodes such as dispersive electrodes and MFE's. Specifically, if one were to specify an aluminum wire of 15 square inches in diameter and a "length" of 0.0005", one would have specified the aluminum foil conductor of a dispersive electrode as described in Netherly et al.

For a simple large biomedical electrode of the prior art with a homogenous and isotropic conductor surface (such as 0.0005" Al foil), the contact impedance will be inversely proportional to the surface area of the electrode that is adhered to the skin. While this inverse proportionality is not exact due to the inhomogeneity of human tissue, it is a reasonably linear inverse relationship. This phenomenon has also been documented regarding the size (or cross sectional area) of defibrillation, MFE, and ECG electrodes. It is known that as a normal metal foil biomedical electrode is peeled back from the skin, the contact resistance will increase proportionally. This effect can be observed with any biomedical electrode using a homogenous conductor element.

Resistance of a conductor may be increased by reducing its cross sectional area, and in the case of a metal foil biomedical electrode, this simply amounts to a reduction in surface area. For the electrodes of the present invention, as embodied for example in the electrodes shown in FIGS. 1 and 2, however, the unexpected result is that this reduction of surface area is accomplished on a strictly localized basis around the periphery of the electrode's conductor.

The embodiment of FIG. 2 has been tested and showed significant reductions in the edge effect due to 6 consecutive 360 Joule defib shocks, the periphery of the Ag/AgCl ink layer has been almost totally (98%–99.9%) covered with thermal wax dots serving as a screen 46, which are highly resistive in nature and permit NO direct current flow. The result is an electrode conductor with many microscopic "pinholes" in the wax which form very many, very small, high resistance pathways. In this example, the increase in resistance at the edge of the conductor has been accomplished by the limitation of surface area alone. The resistance of the metal ink at the pinholes is exactly the same as if the entire surface of the conductor were bare metal ink, because the increase in resistance has come only through a localized reduction in cross sectional area. In a very true and literal sense, therefore, the "resistive means" of this embodiment are unique in that they have no separate physical existence apart from the interface between the conductor and the conductive adhesive which existed before the thermal wax dots were added to the conductor surface.

In a similar fashion, the embodiments like that in FIG. 1 have demonstrated a significant reduction in edge effect under similar defibrillation currents, and these constructions all consist of some highly resistive plastic film or screen 26 embedded in the actual body of the conductive adhesive layer 18 to make higher resistance pathways around the circumference of the conductor. These pathways may take the form of many small discrete holes or pores in screen 26, or alternatively a single or a few large holes in screen 26 which have a complex or convoluted border geometry. Once again, the increase in resistance comes solely through the reduction of the cross sectional area of the conductive adhesive, to create small higher resistance pores or narrow channels penetrating the thickness of the adhesive layer itself. In this case, one may also say that there is no alteration in the resistance of the adhesive by any means involving a change in adhesive chemistry and/or the addition of high resistance fillers, and as such the "resistive means" once again do not exist apart from the conductive adhesive itself.

Another embodiment for the electrode shown in FIG. 1 could be a thin plastic film with a large center hole, (corresponding to the bare metal center of the Netherly Electrode of Netherly et al.) and around that a series of circular and concentric holes of different diameter corresponding to the lossy dielectric layers of the Netherly Electrode of Netherly et al. In addition, there could be a gradation of hole sizes ranging from larger in the middle to very small at the periphery. This plastic film could be colored for purposes of visibility as seen in FIG. 3, and after perforation will be used as a scrim layer in the coating of a typical hydrophilic, ionically conductive adhesive identified above. Alternatively, the scrim 26 could be a non-conductive film with a central hole and a "sunburst" shape cut out. In this embodiment, there are no distinct holes but a symmetrical pattern of an extended inner perimeter.

As far as conductor shape for layers 14, 16, 17 or 34, 36, 37; because of the severity of the current density that is trying to be reduced, one could use a totally circular design, with some minor protuberance off of one side of the silver ink conductor for the attachment of the leadwire.

Preferably, one could have the layer 18 or 38 of hydrophilic ionically conductive adhesive which will extend beyond the silver ink conductor layer by some amount between 2 mm and 25 mm, and preferably between 4 mm and 18 mm.

In the case of defibrillation, skin injuries often looking like burns are the overwhelming rule rather than the rare exception. All available evidence points to these lesions as most likely being ruptured and coagulated subcutaneous capillaries that could not survive the intense current density of the defibrillation pulse. The present invention uses a combination of the change in impedance in the mammalian epidermis due to the presence of a hydrophilic adhesive extending beyond the conductor layers 14, 16 and 17 with a reduction of Z-axis cross sectional conductor area in the conductive adhesive layer 38, or with a reduction in Z-axis cross sectional area of the conductive interface between layers 17 and 38, or with a reduction in the X-Y plane of cross sectional area of the conductive layers 14, 16, and 17 to reduce the edge effect to reduce this burn problem, and the subsequent pain that accompanies this "burn". Edge effect reduction can also result in increased comfort of external cardiac pacing, which at present is so unpleasant that present medical practice favors even invasive measures of an insertion of a catheter over placement of an external, noninvasive pacing electrode.

In a more mathematically rigorous exposition of this invention, but without being limited to a particular theory, the resistance of a conductor with a uniform cross-sectional area is given by the equation:

$$R = (\zeta \cdot L)/A$$

where R is expressed in Ohms., where $\zeta$ is the intrinsic resistivity (in Ohm-cms) of the ionic or electronic conductor material, L is the length of the conductor, and A is the cross sectional area of the conductor.

Based on the above equation, it may be seen that there are three ways to change the resistance of a cylinder of a conductive material.

Firstly, the intrinsic resistivity $\zeta$ of a conductor may be changed by chemically altering the composition of the conductor material; so as to either increase or decrease the resistivity of the material by the use of more or less conductive fillers, more or less conductive alloys of various metals, higher or lower concentrations of ionic salts, shorter or longer molecular length, and other modifications known to those skilled in the art.

Secondly, the length L of the cylindrical conductor may be physically changed, with an increase in conductor length resulting in an increase in the resistivity of the cylindrical conductor as a whole.

Thirdly, the cross-sectional area A of the cylinder may be physically changed, with a decrease in cross-sectional area resulting in an increase of the resistance of the cylindrical conductor as a whole.

The present invention relies upon alteration of the variable A, which is previously unknown in the art. For example, Netherly et al.'s use of a lossy dielectric material at the periphery of an electrode relies on the alteration of L and $\zeta$; with L being controlled by the coating thickness (or conductor length, relative to the Z-axis current flow) of the lossy dielectric ink, and with $\zeta$ being controlled by the exact chemical mixture of the ingredients of a certain ink formulation. The disclosure of U.S. Pat. No. 5,571,165 (Ferrari et al.) also relies on the alteration of L and $\zeta$; by the selection of various conductive materials such as carbon, silver, and silver chloride, and also by the coating thickness of some of these materials. Similarly, the previously identified article by Wiley and Webster describe approaches based on only an alteration of L or $\zeta$ alone.

The physical embodiment of the variation of L concerned a disk made up of a conductive material, and the thickness of this disk varied from a small value (low Z-axis resistivity) at the center of the electrode to a high value (high Z-axis resistivity) at the periphery of the electrode. The drawback to this design was that it was convex in shape, and thus not useful for making good contact with mammalian tissues.

The physical embodiment of the variation of $\zeta$ consisted of a flat disk, which was made up of a material of variable intrinsic resistivity, and it was noted that such a variation in a solid material would be "rather difficult to achieve".

Also similarly, the previously identified article by Kim et al. describes a peripheral Z-axis adhesive resistivity construction based on the variation of $\zeta$, involving a uniformly conductive plate and an array of annular gel segments, in which each segment had a different intrinsic resistivity, with the lowest resistivity being in the center and the highest resistivity being at the periphery of the electrode. While this construction would be capable of making good contact with mammalian tissues, it would involve many separate gel formulations and an incredibly complex manufacturing process, or the need for invention of a chemical process which could produce a gel coating which had a smoothly varying intrinsic resistivity.

Elegantly but unexpectedly, the present invention, with the use of a single, isotropic hydrophilic ionically conductive adhesive formulation, which contains screen 26 with either a multiplicity of small, discrete holes, or a single or small number of large holes with a complex or convoluted border geometry, makes feasible such a peripheral Z-axis adhesive resistivity gradient, which affects the variable A in the above equation.

This is accomplished in an unexpected way by the highly localized control of the cross sectional conductor area A, in either the Z-axis direction in the conductive adhesive layer 18 or 38, or in the Z-axis direction at the interface of conductor 17 or 37 and the adhesive 18 or 38. It may also be accomplished by limiting the conductor width and thickness of conductor layers 14, 16, and 17 and printing or otherwise arraying these conductors in geometric and/or fractal patterns which will effectively create a radial impedance gradient in these conductor layers, as described above in the various embodiments.

Further embodiments of the invention are described in the following examples.

EXAMPLE 1

A Transpore™ tape backing material commercially available from Minnesota Mining and Manufacturing Company (3M) of St. Paul, Minn. made of polyethylene with a small percent of ethylene vinyl acetate has the following physical characteristics: 0.102 to 0.127 mm film thickness, containing an orthogonal grid of perforations 0.020 to 0.026 mm diameter of irregular shape, and the perforations are 1 mm apart on the grid. Using two cylindrical stainless steel electrodes, the resistance of a 0.03 N $KClO_4$ solution placed between the circular faces was measured with and without the presence of the perforated sheet. The values measured were 0.69 and 17.7 ohms respectively, which demonstrates that Z-axis resistance can be readily controlled by the introduction of a perforated highly resistive material in an ionically conductive medium. Now from the formula $R=(\zeta \cdot L)/A$, $A=(\zeta \cdot L)/R$. If the area constituted by the perforations through which the current passed is designated by A', and that without the perforated sheet as A, then $A'/A=(0.69/17.7)100=4\%$. This is the percent of open cross sectional conductor area constituted by the perforations in the sheet that is located between the faces of the steel electrode cylinders. The ratio of A/A' may be used to specify and/or characterize the performance of such perforated highly resistive films. This value agrees well with physical measurements of the individual pore size of the Transpore™ backing which were measured at average size of approximately 0.23 mm with a 1 mm spacing on an orthogonal grid. Per square mm of surface area, then, the percent of open cross sectional conductor area would be $((0.23/2)^2*3.14159)*100=4.1\%$. It has thus been demonstrated that the increase in electrical resistivity due to the reduction of cross sectional conductor area of an ionically conductive solution or medium correlates well with the actual measured physical reduction of this conductor area.

EXAMPLE 2

Figure 4:
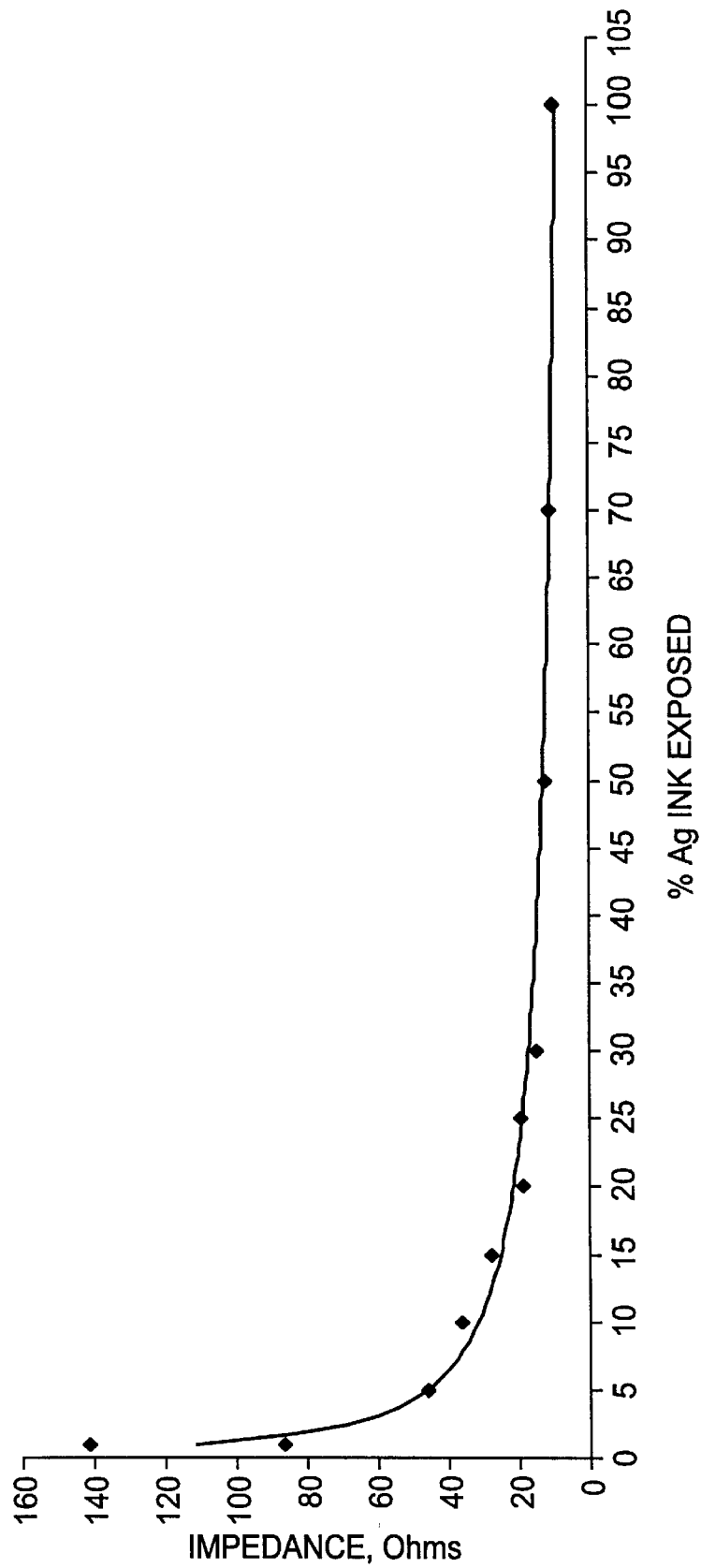
FIG. 4 is a graph of Impedance vs. Exposed Silver Ink.

Samples of PET film were coated with a commercially available silver ink (No. 301S from Ercon of Waltham, Mass.), and then dried. Portions of the ink surface were then overprinted with small dots by means of a thermal wax printer (Phaser III printer purchased from Tektronix), which functions in the same general way as an inkjet printer, except that the "ink" used is a thermoplastic colored wax rather than a water soluble dye. The wax itself is a highly resistive material, and samples were printed using a halftone pattern at various density levels to create a range of cross sectional conductor areas on each sample. These samples were then laminated to the hydrophilic ionically conductive adhesive described in U.S. Pat. No. 4,848,353 (Engel), and pairs of samples of identical cross sectional conductor areas were then laminated together with their adhesive faces touching. Defibrillation shocks were then sent through these pairs of samples, and the impedance was measured. The data is shown below in tabular and graphic form as FIG. 4, and as can be seen, there is a high degree of correlation ($R^2$=0.971) between the halftone density area and the resulting impedance measured during the passage of a defibrillation shock. It has thus been demonstrated that the increase in electrical resistivity due to the reduction of cross sectional conductor area upon an electrical conductor's surface correlates well with the actual measured physical reduction of this conductor area.

TABLE 2

| % Ink Coverage | Impedance |
|---|---|
| 0 | 9.7 |
| 30 | 11.14 |
| 50 | 12.47 |
| 70 | 14.61 |
| 75 | 19.53 |
| 80 | 18.4 |
| 85 | 27.97 |
| 90 | 36.11 |
| 95 | 46.04 |
| 100 | 141.21 |
| 100 | 86.44 |

EXAMPLE 3

Figure 5:
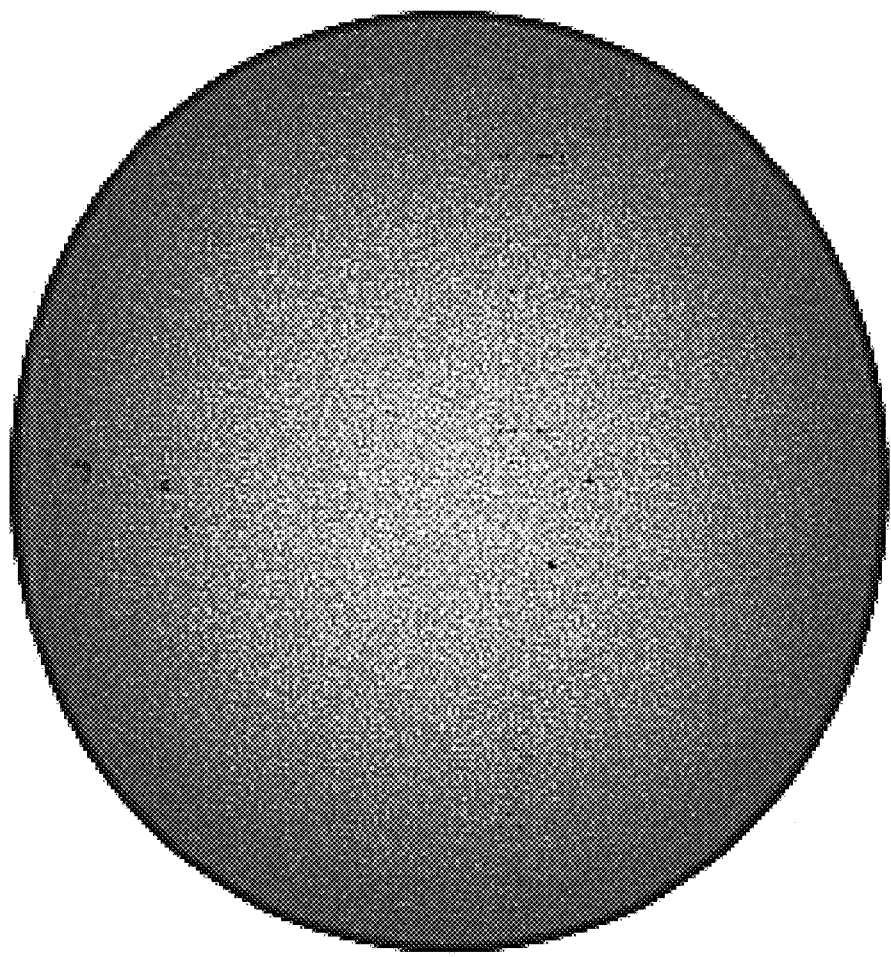
FIG. 5 is a digital image of an experimental gradient printing of an embodiment of the invention.

Using the materials and methods described in Example 2, a wax gradient design was printed using a QuarkExpress presentation software package commercially available from Quark, Inc. This design was printed on an identical silver ink conductor that was circular in shape and 12.7 cm (5 inches) in diameter, using the same thermal wax printer. A layer of the same conductive adhesive was then laminated to the printed conductor, and a control sample was made up using a 12.7 cm (5") round silver ink conductor, (with no printing on it) which was similarly laminated to a layer of conductive adhesive. FIG. 5 shows the appearance of the shaded image as was printed on the experimental sample.

Figure 6:
FIG. 6 is a subtracted thermogram digital image of a prior art electrode applied to a piece of beef.
Figure 6:
Figure 7:
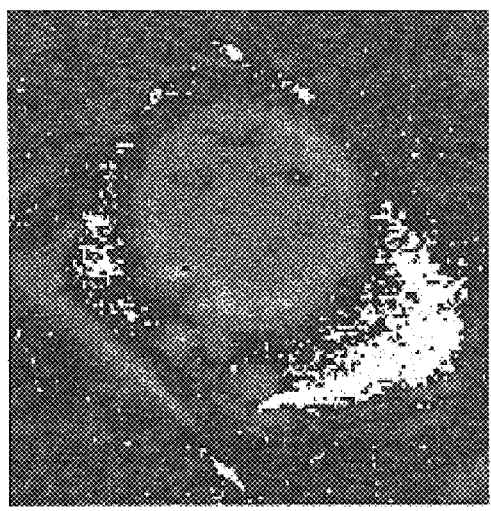
FIG. 7 is a subtracted thermogram digital image of an electrode of the invention applied to the same piece of beef.
Figure 7:

The two samples were then separately tested on bovine mammalian tissue (a 1.92 kg (4.25 lbs.) chuck roast) which was attached by means of a ground plane to one lead of a PhysioControl Lifepak 9 defibrillator (Redmond, Wash.). The other lead was attached to the center of each electrode, which was placed on the center of the beef tissue. A series of six 360 Joule shocks was then administered to the beef as quickly as possible, and the electrode was removed from the beef immediately after the last shock. A thermal image of the heat buildup in the beef was taken with an Agema 470 IR camera. To reduce error and thermal artifact, "before" thermal images were taken of the beef at room temperature before the start of each test, and full frame image subtractions were done with the "after" images. The two subtracted images are shown in FIGS. 6 and 7 with FIG. 6 showing the control and FIG. 7 showing that the heating in the beef due to the current distribution caused by the edge effect is spread over a much larger percentage of the electrode's surface than as seen in FIG. 6. It has thus been demonstrated that the increase in electrical resistivity due to the reduction of cross sectional conductor area upon an electrical conductor's surface can be used to create a biomedical electrode which can more evenly distribute current in mammalian tissue.

EXAMPLE 4

Figure 8:
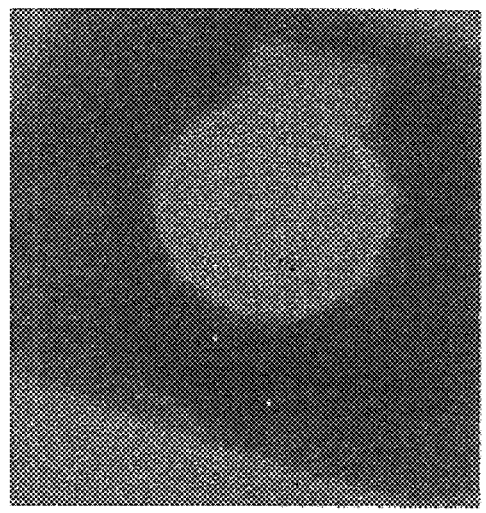
FIG. 8 is a thermogram digital image of an electrode of the invention applied to the same quantity of solid gel.
Figure 9:
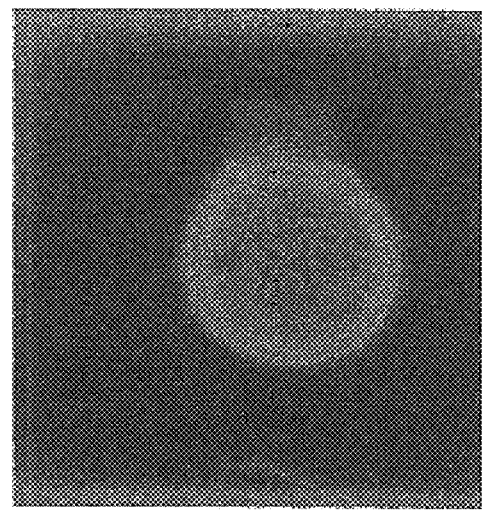
FIG. 9 is a thermogram digital image of a prior art electrode applied to a quantity of solid gel.

To simulate mammalian tissue in a more convenient manner in further experiments, a mass of the composition of Red Dot™ solid gel, disclosed in U.S. Pat. No. 4,406,827 (Carim), the disclosure of which is incorporated by reference herein weighing about 10.88 kg (24 pounds) was placed in a plastic tub. A stainless steel plate was placed in the bottom of the tub to act as a ground plane, and this was connected to the ground lead wire from a Physio Controls LifePak 9 defibrillator. An experimental electrode was then made up consisting of a 11.43 cm (4.5") diameter round silver ink conductor, to which was concentrically laminated a 12.7 cm (5") diameter layer of conductive adhesive. In the preparation of this adhesive, a circular annulus of Transpore™ backing with an outer diameter of 12.7 cm (5") and an inner diameter of 10.16 cm (4") was cured in place in the adhesive. This electrode was then placed on top of the solid gel block that simulated mammalian tissue and it was connected to the other lead wire of the defibrillator. A series of six 360 Joule pulses was sent through the electrode as quickly as possible, and the electrode was then removed from the solid gel block and the temperature was recorded as before. As a control, a 11.43 cm (4.5") diameter silver ink conductor was laid directly on the solid gel in another experiment, and the testing described above was repeated. The results are shown in FIGS. 8 and 9, respectively, side by side in two thermograms which have been scaled identically. It can be seen there is definitely a broadening of the heating in the image of FIG. 8 compared with the image of FIG. 9 which indicates a greater degree of current dispersion in the solid gel block. This results correlates with a reduction of edge effect in mammalian tissue at the interface with a biomedical electrode of the present invention.

It has thus been demonstrated that the increase in electrical resistivity due to the reduction of cross sectional conductor area within a hydrophilic ionically conductive adhesive can be used to create a biomedical electrode which can more evenly distribute current in an aqueous ionic medium similar to mammalian tissue.

EXAMPLE 5

Figure 10:
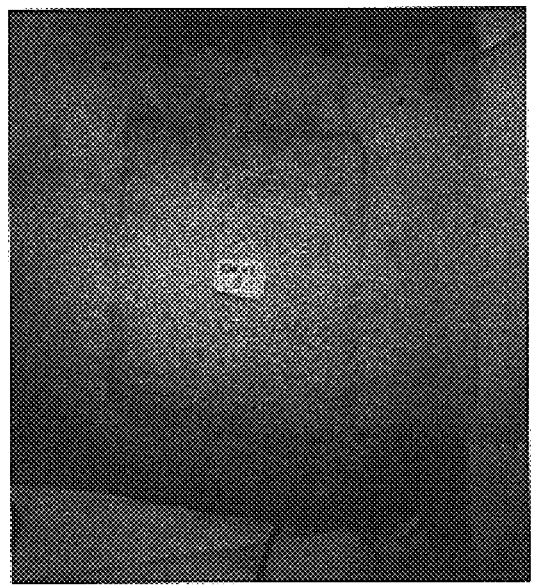
FIG. 10 is a digitized photograph of porcine mammalian tissue after a defibrillation shock using a prior art electrode.
Figure 11:
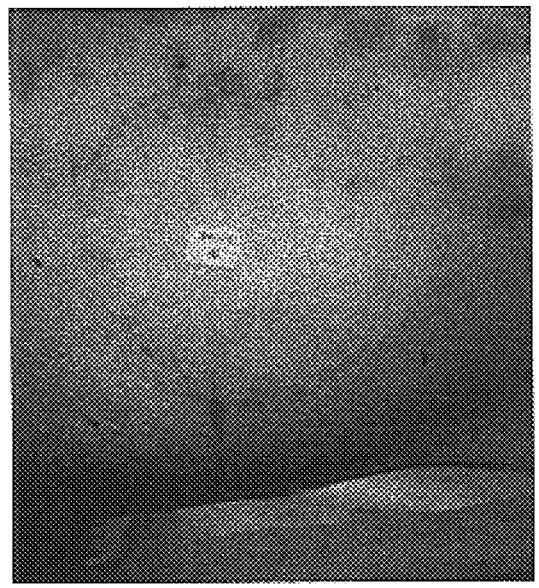
FIG. 11 is a digitized photograph of a different location of porcine mammalian tissue after a defibrillation of shock using an electrode of the invention.

A commercially available defibrillation multifunctional electrode ("Quantum Edge" No. 3010188-001 by Contour, of LaVergne, Tenn., USA; based on the disclosure of U.S. Pat. No. 5,571,165 (Ferrari)) was tested simultaneously with a universally functional biomedical electrode identical to the one described in Example 4 above. The test was conducted on the skin of an anesthetized pig using 2 shocks at 360 Joules from a Physio-Control LifePak 9 commercial defibrillator, with one lead of the defibrillator being connected to the Quantum Edge product, and the other to the Example 4 electrode. The test compared the erythyma/burn produced on the porcine skin. Two digital images of photographs are shown in FIGS. 10 and 11, respectively, and the photos were taken approximately 4 minutes after the defibrillation shock. As can be seen from the photos, the round electrode of the present invention in FIG. 11 produced noticeably less erythyma at 4 minutes than the erthyma produced in the commercially available product seen in FIG. 10, and what erythyma was produced in the Example 4 electrode was spread over a much broader area than the edge of the interface between tissue and electrode. These results are consistent with the results from the previous thermography experiments of the above Examples. Moreover, the erythyma appearing in the tissue imaged in FIG. 11 faded completely within 20 minutes, whereas the erythyma produced by the Quantum Edge product in the tissue imaged in FIG. 10 remained readily apparent after 20 minutes.

Figure 12:
FIG. 12 is a digitized photograph of an histology section of the porcine tissue of FIG. 10, with blue circles added.
Figure 13:
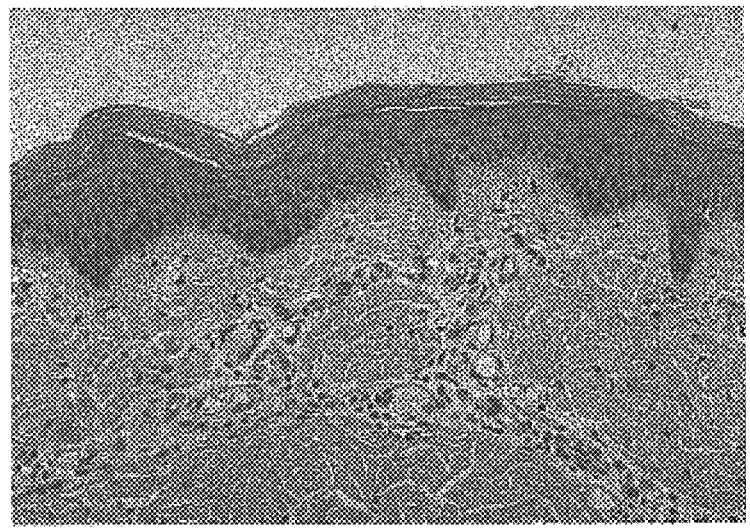
FIG. 13 is a digitized photograph of an histology section of the porcine tissue of FIG. 11.

In addition to the obvious visual difference between the two patterns seen in FIGS. 10 and 11, histology sections were taken from the skin of the pig where the erythymas occurred. The sections are shown in FIG. 12 and FIG. 13, and at the microscopic level there are significant differences between the two samples. The sample from the Quantum Edge site (FIG. 12) shows a complete absence of stratum corneum in some locations due to sudden heating and vaporization of the tissues, and this was accompanied by a very obvious burning smell at the time the defibrillation shock was administered. In addition to this, there is coagulated blood (circled in blue) in some of the small subcutaneous capillaries due to the high current density in the porcine tissues.

By contrast, the sample from this invention in FIG. 13 shows a still intact layer of stratum corneum and no evidence of coagulated blood in the smaller vessels.

It has thus been demonstrated that the increase in electrical resistivity due to the reduction of cross sectional conductor area within a hydrophilic ionically conductive adhesive can be used to create a biomedical electrode which can more evenly distribute current in mammalian tissue, and that this reduction of current can result in a direct and observable reduction in burns with multiple defibrillation shocks of 360 Joules.

Further significant advantages of the present invention are summarized as follows and demonstrates the unexpectedness of the present invention:

i) The present invention uses a simple reduction of the cross sectional area of resistive materials as a resistive element within the electrode structure to create a localized increase in impedance which is almost totally resistive in nature. As a result, a reduction of the maximum current density in mammalian tissues due to edge effect is obtained. This result is obtained which is independent of the frequency and/or waveform of the current being used. As a result, the wave shape of defibrillation and pacing currents are not distorted, and even at electrosurgical frequencies, the current density in mammalian tissues due to edge effect can be reduced.

ii) For the embodiment of FIG. 1, because the resistive element resides in the conductive adhesive layer 18 and not on the surface of the conductor, it does not lower the available conductor surface needed for the electrochemical reactions to keep the electrochemical polarization low.

iii) For the embodiments of the present invention involving a reduction in cross sectional conductor area in the X-Y plane of the conductor, the usage of expensive conductive inks in one or more layers can be minimized so as to achieve a lower manufacturing cost for the electrode.

The invention is not limited to the above embodiments. The claims follow.

What is claimed is:

1. A universally functional biomedical electrode, comprising:

an electrode element having an electronic conductor surface;

a conductive adhesive material in contact with the electrode element; and a resistive element that reduces edge effect, wherein the reduction of edge effect results from structures selected from the group consisting of:

(1) limiting the cross-sectional area of the electronic conductor surface by selectively blocking conduction from the electronic conductor surface into the conductive adhesive material with a highly resistive material as a gradient from the center toward the periphery;

(2) limiting the cross-sectional area of the electronic conductor surface in the X-Y plane of the electrode element via printing or other contacting of conductive material as a gradient from the center out words towards a perimeter of the electrode; and (3) combinations thereof.

2. The electrode of claim 1, wherein the electrode redistributes current employing the equation:

$$R=(\zeta \cdot L)/A$$

where R is resistance expressed in Ohms, where $\zeta$ is the intrinsic resistivity (in Ohm-cms) of an ionic or electronic conductor in the electrode, L is the length of the conductor, and A is the cross sectional area of the conductor, wherein A is variable in the electrode.

3. The electrode of claim 1, wherein the conductive adhesive material is adapted to be placed in contact with mammalian tissue, the conductive adhesive material extending beyond the perimeter of the electronic conductor surface in the electrode.

4. The electrode of claim 1, wherein the conductive adhesive material is hydrophilic.

5. The electrode of claim 3, wherein the quantity of conductive adhesive material that extends beyond the electronic conductor surface ranges from about 2 mm to about 25 mm.

6. The electrode of claim 1, wherein the structure limiting the cross-sectional area of the electronic conductor surface by selectively blocking conduction with a highly resistive material comprises a screen made by printing a highly resistive or electronically insulating ink onto a major surface of the electronic conductor surface in the electrode.

7. The electrode of claim 6, wherein the printing generates a pattern selected from the group consisting of an exact printed replica of a physical screen where the pores are defined by the absence of the highly resistive ink, a halftone pattern, an essentially random pattern of ink dots, and a small number of holes with a complex or convoluted border geometry, and combinations thereof.

8. The electrode of claim 7, wherein a percentage area of the electronic conductor surface containing the screen ranges from about 2% to about 60%.

9. The electrode of claim 1, wherein the electrode element further comprises a backing layer supporting the electronic conductor surface, and wherein the structure that limits cross-sectional area of the electronic conductor surface in the X-Y plane of the electrode element occurs within the electronic conductor surface in that a design of conductive material is printed in a pattern originating from a central location and extending outward toward a periphery of the electrode.

10. A biomedical electrode, comprising:

at least one electronic conductor in contact with an ionically conductive material that interfaces mammalian tissue for exchanging electromagnetic energy, the ionically conductive material containing:
  (a) at least one highly resistive material, having an impedance that is substantially higher than that of the ionically conductive material;
  (b) at least one of the said highly resistive material(s) being substantially coplanar with a major surface of the conductor; and
  (c) the highly resistive material having a geometry, shape and apertures selected to alter the current density profile reaching an interface between the electrode and mammalian tissue;

wherein there is direct contact between the ionically conductive material and the highly resistive material, and there is an electrolyte between the highly resistive material and the tissue.

11. The electrode of claim 10, wherein the highly resistive material and the ionically conductive material extend beyond the contour of the edge of the major surface of the electronic conductor, and where the electrolyte is hydrophilic.

12. A biomedical electrode, comprising:

at least one electronic conductor in contact with an ionically conductive material that interfaces mammalian tissue for exchanging electromagnetic energy, the ionically conductive material containing:
  (a) at least one highly resistive material, having an impedance that is substantially higher than that of the ionically conductive material;
  (b) at least one of the said highly resistive material(s) being substantially coplanar with a major surface of the electronic conductor; and
  (c) the highly resistive material having a geometry, shape and apertures selected to alter the current density profile reaching an interface between the electrode and mammalian tissue;

wherein the highly resistive material is substantially resistive to electrical energy waveforms in the frequency range of 0 to 2 MHz.

* * * * *

UNITED STATES PATENT AND TRADEMARK OFFICE
CERTIFICATE OF CORRECTION

PATENT NO. : 6,701,172 B2
DATED : March 2, 2004
INVENTOR(S) : Katzenmaier, Kevin R.

It is certified that error appears in the above-identified patent and that said Letters Patent is hereby corrected as shown below:

Column 2,
Line 39, delete "A" and insert in place thereof -- a --;

Column 22,
Line 65, delete "out words" and insert in place thereof -- outwards --.

Signed and Sealed this

Sixth Day of July, 2004

JON W. DUDAS
*Acting Director of the United States Patent and Trademark Office*